United States Patent
Ghelli et al.

(10) Patent No.: US 7,621,885 B2
(45) Date of Patent: Nov. 24, 2009

(54) SET OF UNITS FOR A DEVICE INTEGRATED IN AN EXTRACORPOREAL BLOOD CIRCUIT

(75) Inventors: Nicola Ghelli, S. Pietro In Casale (IT); Edgardo Costa Maianti, Mirandola (IT); Roberto Balanzoni, San Giovanni Del Dosso (IT)

(73) Assignee: Eurosets S.r.l., Medolla (IT)

( * ) Notice: Subject to any disclaimer, the term of this patent is extended or adjusted under 35 U.S.C. 154(b) by 0 days.

(21) Appl. No.: 11/802,593

(22) Filed: May 24, 2007

(65) Prior Publication Data

US 2007/0293804 A1 Dec. 20, 2007

(30) Foreign Application Priority Data

Jun. 20, 2006 (IT) .......................... MI2006A1188

(51) Int. Cl.
*A61M 37/00* (2006.01)

(52) U.S. Cl. ..................... 604/6.15; 604/6.09; 604/6.14

(58) Field of Classification Search ................ 604/6.09, 604/6.14, 6.15, 326, 319, 322; 137/355.18
See application file for complete search history.

(56) References Cited

U.S. PATENT DOCUMENTS

| | | | |
|---|---|---|---|
| 3,929,414 A | 12/1975 | Leonard | |
| 4,819,636 A * | 4/1989 | Gerich et al. | 606/122 |
| 5,304,164 A | 4/1994 | Lindsay | |
| 6,468,473 B1 * | 10/2002 | Lindsay | 422/45 |
| 7,201,870 B2 * | 4/2007 | Olsen et al. | 422/44 |
| 2004/0065626 A1 * | 4/2004 | Woo | 210/767 |

FOREIGN PATENT DOCUMENTS

| | | |
|---|---|---|
| EP | 0 705 610 A | 4/1996 |
| EP | 0 885 618 A1 | 12/1998 |
| EP | 1 382 358 A | 1/2004 |
| EP | 1 464 349 A | 10/2004 |
| WO | WO 99/22785 A | 5/1999 |
| WO | WO 00/47266 A | 8/2000 |

* cited by examiner

*Primary Examiner*—Tatyana Zalukaeva
*Assistant Examiner*—Susan Su
(74) *Attorney, Agent, or Firm*—Modiano & Associati; Albert Josif; Daniel J. O'Byrne

(57) ABSTRACT

A set of units for a device integrated in an extracorporeal blood circuit, comprising a cardiotomy reservoir which is provided with elements adapted to provide a monolithic coupling selectively with identical complementary elements of a venous reservoir and a venous bag.

8 Claims, 6 Drawing Sheets

SET OF UNITS FOR A DEVICE INTEGRATED IN AN EXTRACORPOREAL BLOOD CIRCUIT

The present invention relates to a set of units for a device integrated in an extracorporeal blood circuit.

BACKGROUND OF THE INVENTION

It is known that the extracorporeal blood circuit established during certain surgical procedures substantially comprises units through which the blood is intended to flow, and the first unit that the blood encounters as it exits, by means of a cannula, from a vein of a patient is a container which can have rigid or flexible walls and is known as "venous reservoir" and "venous bag" respectively.

Such venous reservoir or bag, besides receiving blood directly from the patient, is connected to an additional container, known as cardiotomy reservoir, which is designed to receive and filter the blood collected on the operating field.

The blood is drawn from the venous bag or reservoir by means of a pump and is sent to a heat exchanger, which regulates the temperature, to an oxygenation unit for correct addition of oxygen, and finally returned to the patient via an arterial line which is provided with a suitable filter.

The units around the operating field are therefore numerous, with a presence which runs the risk of compromising or at least reducing the freedom of action of the operators, and therefore there is a tendency to reduce their bulk by integrating different units in a single device, achieving the additional advantage of reducing priming, i.e., the amount of blood for filling the circuit.

SUMMARY OF THE INVENTION

It is from this standpoint that the invention has the aim of providing a set of units particularly adapted to constitute an integrated device to be inserted in an extracorporeal blood circuit.

This aim is achieved by a set of units for a device integrated in an extracorporeal blood circuit, according to the invention, characterized in that it comprises a cardiotomy reservoir having means adapted to provide a monolithic coupling selectively with identical complementary means of a venous reservoir and a venous bag.

BRIEF DESCRIPTION OF THE DRAWINGS

Further characteristics and advantages of the present invention will become better apparent from the description of a preferred but not exclusive embodiment thereof, illustrated by way of non-limiting example in the accompanying drawings, wherein.

DESCRIPTION OF THE PREFERRED EMBODIMENTS

Figure 1:
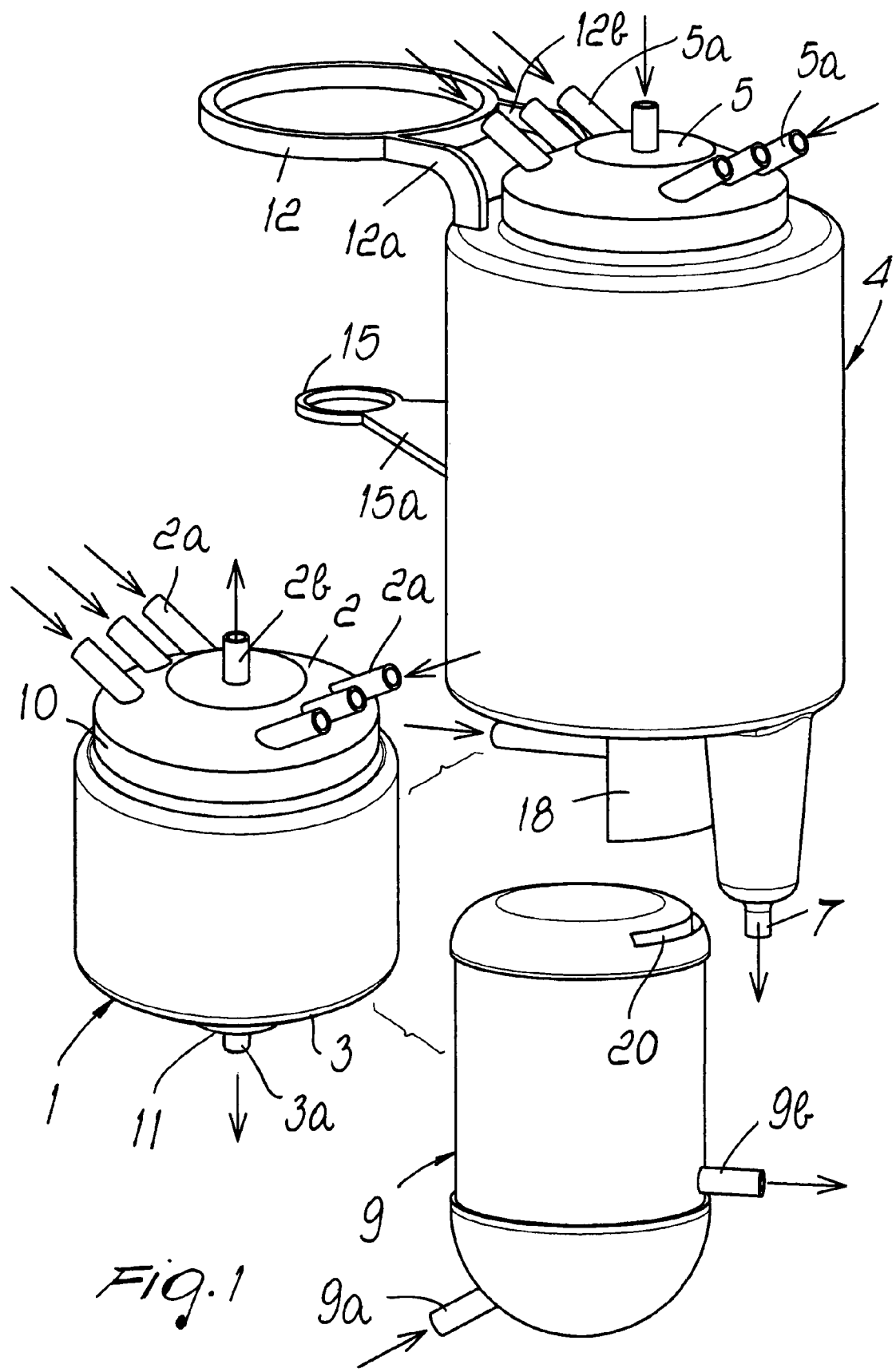
FIG. 1 is a view of three units constituted by a cardiotomy reservoir, a venous reservoir and an oxygenation unit, ready to be associated so as to constitute an integrated device.

With reference to the figures, the reference numeral 1 designates a cardiotomy reservoir, which comprises a lid 2 provided with couplings 2a for the arrival of blood from the operating field and with a coupling 2b for optional withdrawals, and further comprises a bottom 3 provided with a coupling 3a for the outflow of the blood.

Figure 2:
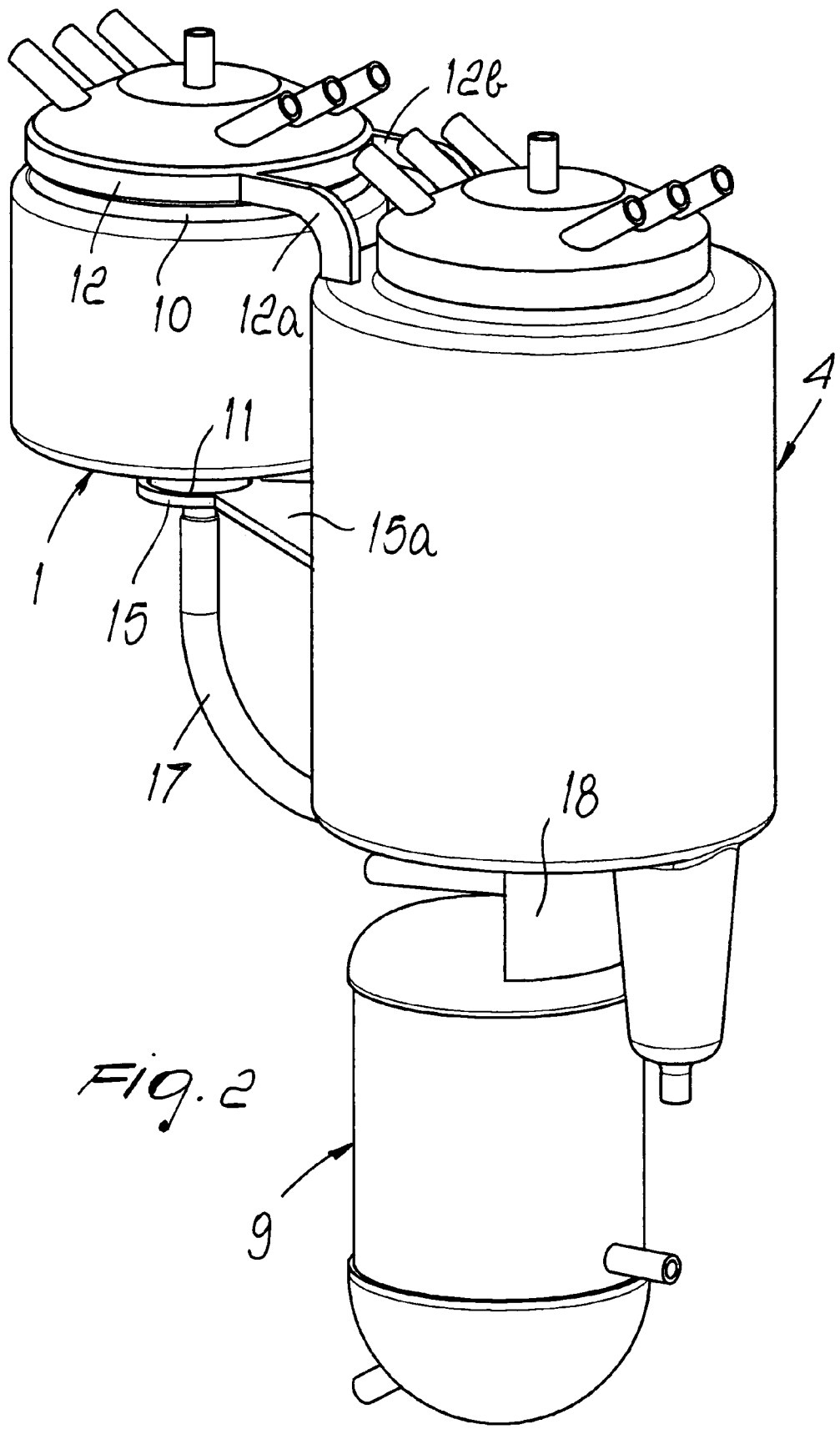
FIGS. 2 and 3 are different views of the integrated device obtained by assembling the units of FIG. 1.
Figure 3:
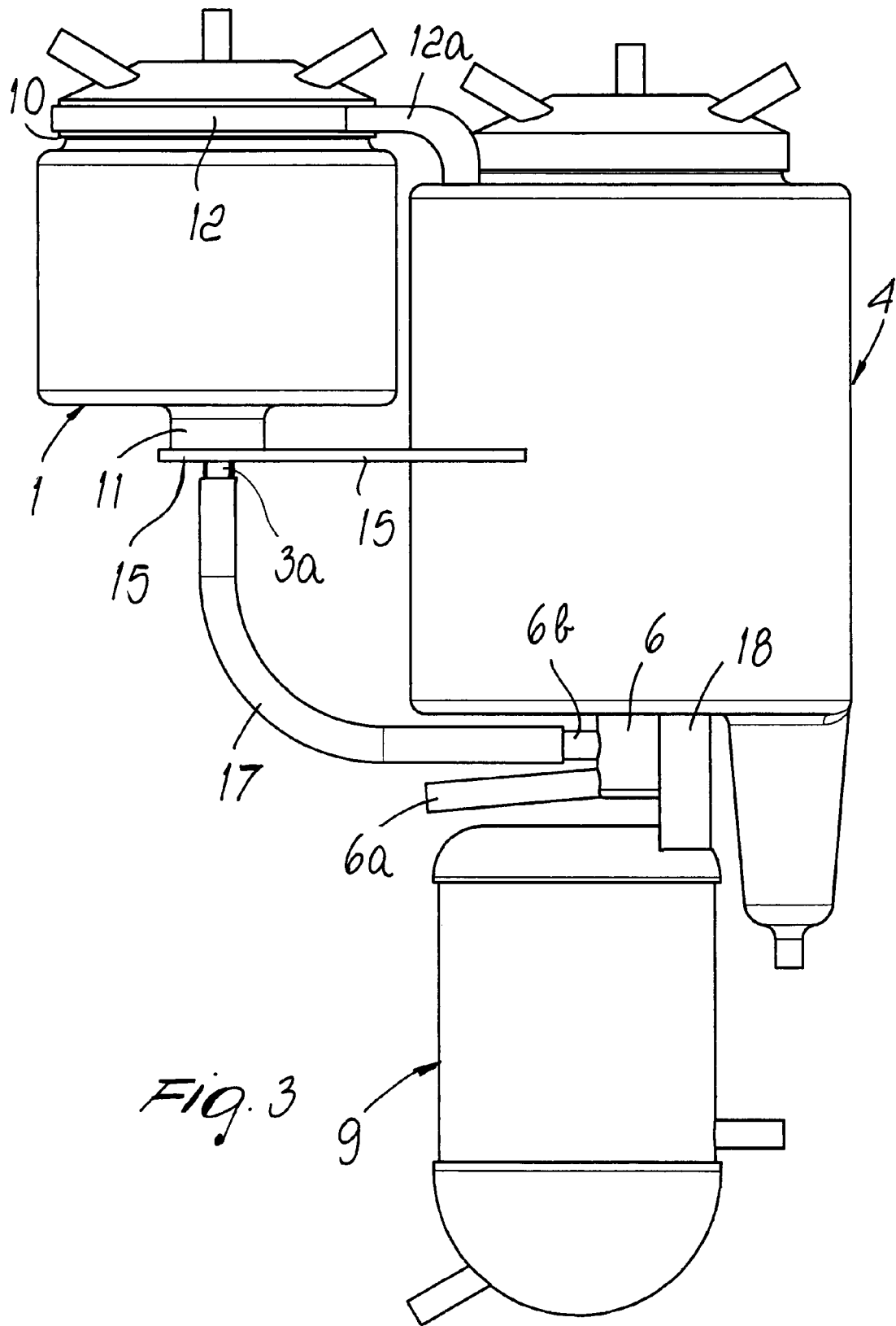

Moreover, in FIGS. 1, 2, 3 the reference numeral 4 designates a venous reservoir, which comprises a lid 5 provided with couplings 5a for the arrival of blood from different points, and further comprises, at the bottom, a connector 6 provided with couplings 6a, 6b for the arrival of blood respectively from the patient and from a cardiotomy reservoir; the reference numeral 7 designates a blood outflow coupling.

Figure 4:
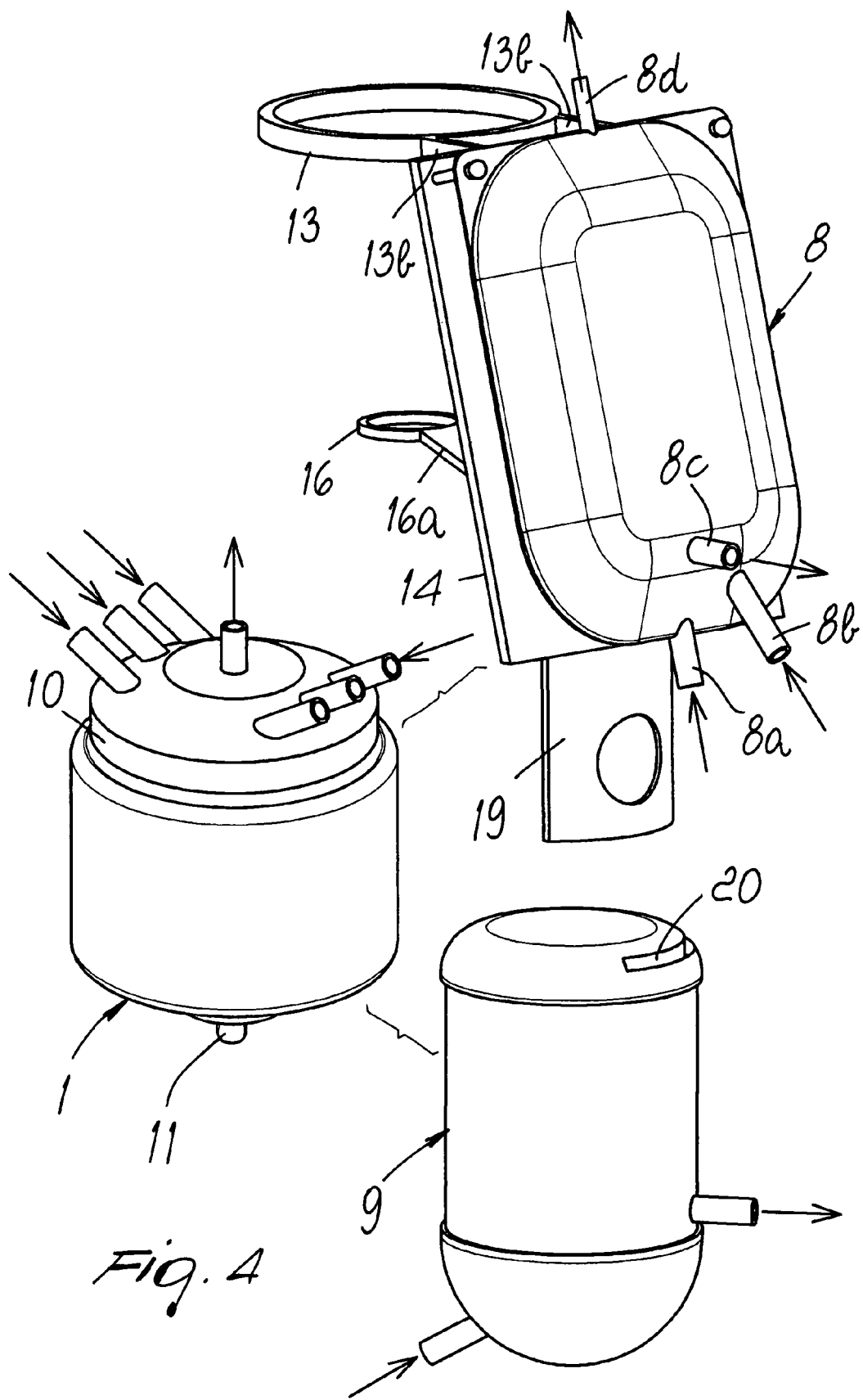
FIG. 4 is a view of three units, constituted by a cardiotomy reservoir, a venous bag, and an oxygenation unit, ready to be associated so as to constitute an integrated device.
Figure 5:
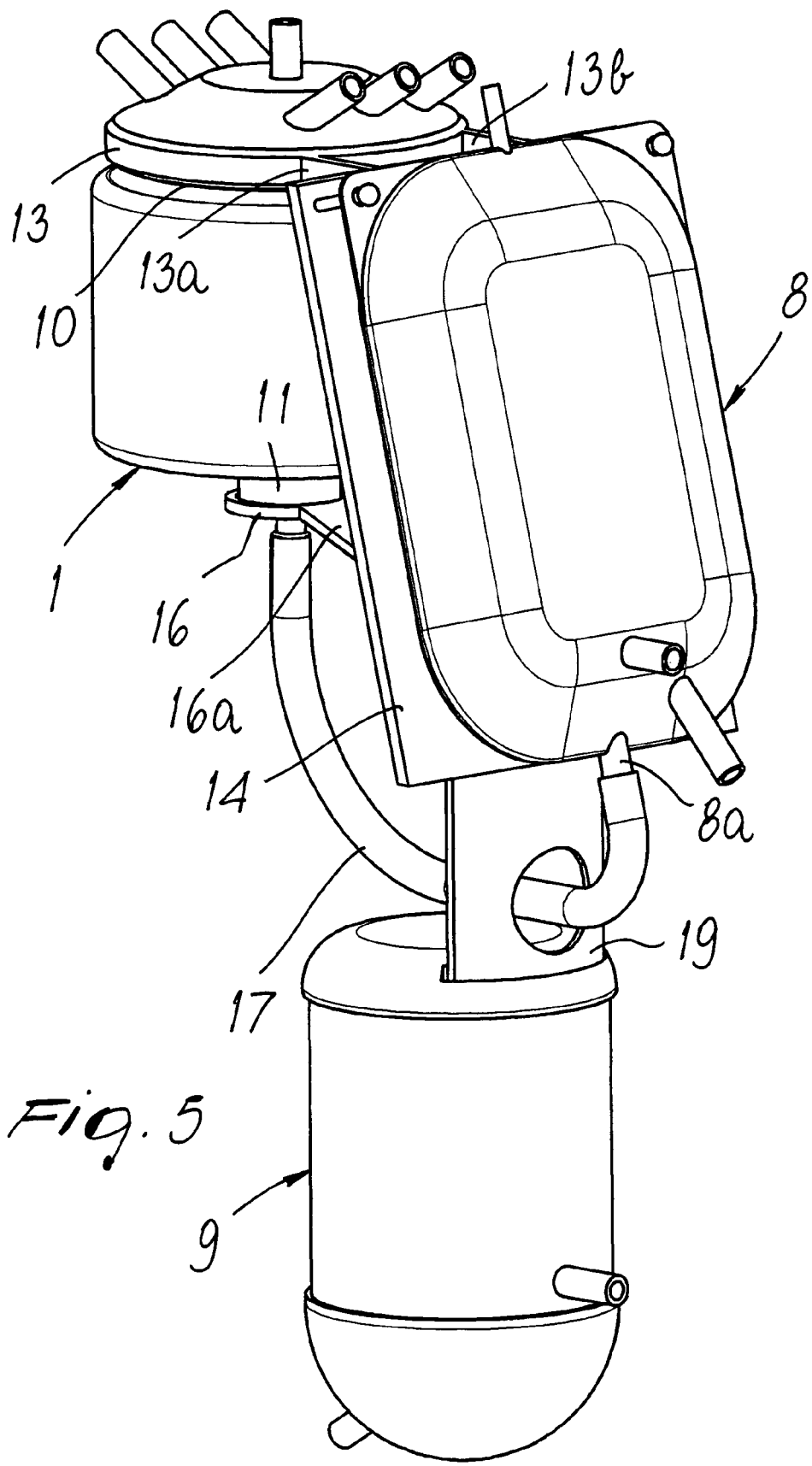
FIGS. 5 and 6 are different views of the integrated device obtained by assembling the units of FIG. 4.
Figure 6:
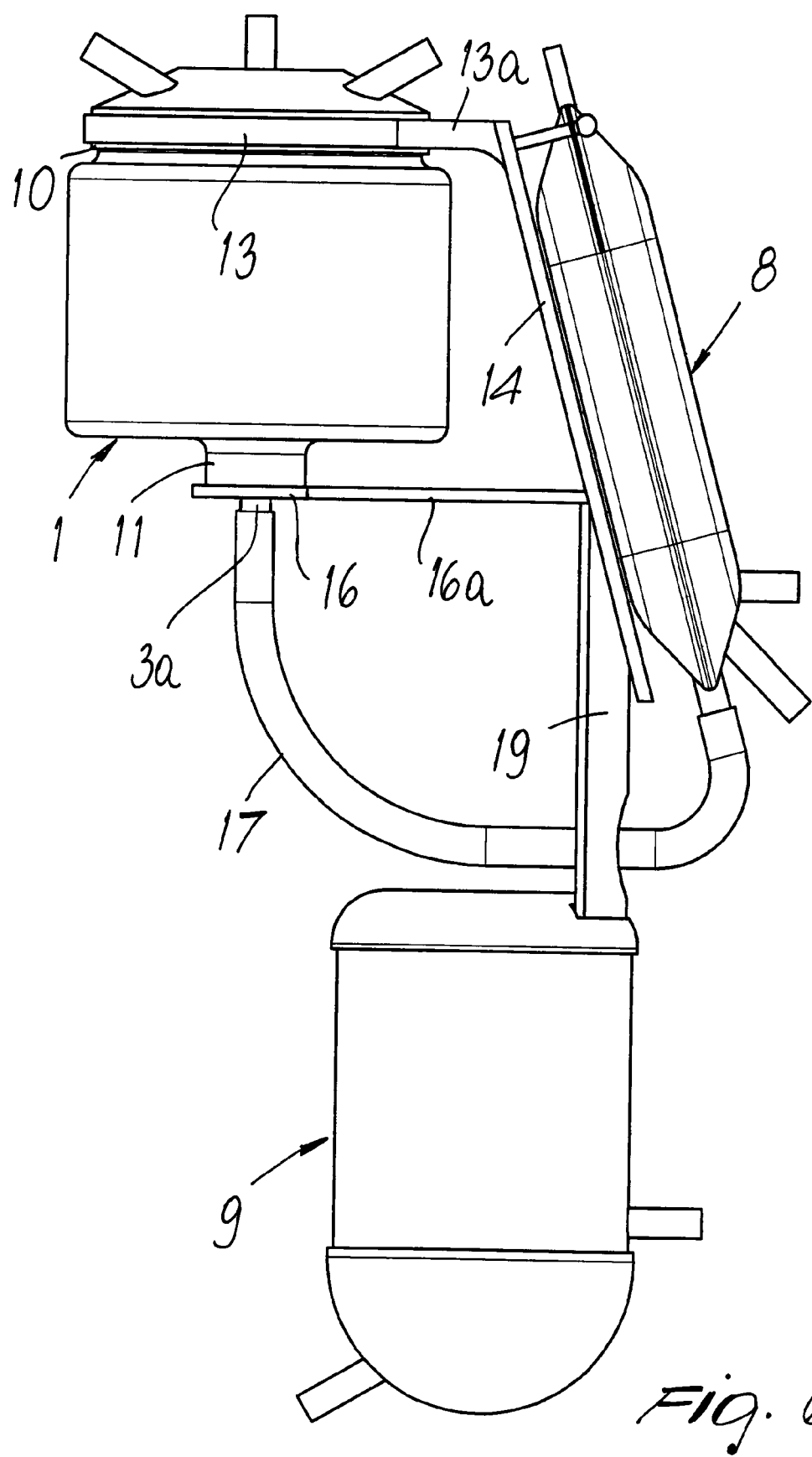

Moreover, in FIGS. 4, 5, 6 the reference numeral 8 designates a venous bag which is provided, proximate to the bottom, with couplings 8a, 8b for the inflow of blood respectively from a cardiotomy reservoir and from a patient, and with a blood outflow coupling 8c; the reference numeral 8d further designates a drain coupling.

Finally, the reference numeral 9 designates an oxygenation unit provided with couplings 9a, 9b for blood inflow and outflow, respectively.

An important feature of the invention consists in that the cardiotomy reservoir 1 comprises two cylindrical portions 10 and 11 which extend respectively from the lid and from the bottom.

The portion 10 is adapted to enter and be locked selectively within a ring 12 which protrudes, by means of tabs 12a, 12b, from the lid of the reservoir 4, and within a ring 13 which protrudes, by means of tabs 13a, 13b, from a rigid base 14 for supporting the venous bag 8.

The portion 11 is adapted to enter and be locked selectively in a ring 15 which protrudes, by means of a tab 15a, from the enclosure of the reservoir 4, and in a ring 16 which protrudes, by means of a tab 16a, from the rigid base 14 for supporting the venous bag 8.

Of course, the means for connecting the cardiotomy reservoir selectively to the venous reservoir and to the venous bag may assume any configuration.

A tube 17 is also provided, which protrudes from the outflow coupling 3a of the cardiotomy reservoir, which is adapted to be connected selectively to the coupling 6b of the venous reservoir 4 and to the coupling 8a of the venous bag 8; the tube 17 is adapted to be blocked when there is no need to supply blood from the cardiotomy reservoir by means of the known scissor-like tool known as clamp, and a tube provided with a tap might be provided in its place.

The venous reservoir 4 and the venous bag 8 are provided with identical means for monolithic connection to the oxygenation unit 9, which comprise the identical tabs 18 and 19 which protrude respectively from the bottom of the reservoir 4 and from the rigid base 14 for supporting the bag 8 and are adapted to enter a slot 20 provided on the lid of the oxygenation unit in order to be locked thereat; of course, said means also may assume any configuration.

Four units have thus been provided which can be used autonomously or can be assembled so as to form two different integrated devices, and the adoption of identical connection means on the venous reservoir and on the venous bag allows to use the same type of cardiotomy reservoir and oxygenation unit for both of said integrated devices.

The described invention is susceptible of numerous modifications and variations besides those mentioned, all of which are within the scope of the appended claims; all the details may further be replaced with other technically equivalent elements.

The disclosures in Italian Patent Application No. MI2006A001188 from which this application claims priority are incorporated herein by reference.

What is claimed is:

1. A set of units for a device integrated in an extracorporeal blood circuit, comprising:
   a cardiotomy reservoir provided with connecting means;
   a venous reservoir provided with complementary connecting means that are shaped complementary to said connecting means of the cardiotomy reservoir;
   a venous bag provided with complementary connecting means thereof that are shaped complementary to said connecting means of said cardiotomy reservoir;
   a tube which protrudes from the cardiotomy reservoir and is adapted to selectively connect to the venous bag;
wherein said venous bag comprises a rigid supporting base thereof and said venous reservoir comprises a lid and an outer enclosure,
said complementary connecting means of the venous reservoir comprises a top ring and a bottom ring that are monolithically connected to said lid and, respectively, to said outer enclosure thereof,
and said complementary connecting means of the venous bag comprises a top ring and a bottom ring that are monolithically connected to said rigid base,
the rings of the venous reservoir being respectively identical to the the rings of the venous bag;
and wherein said cardiotomy reservoir comprises a lid and a bottom, said connecting means of the cardiotomy reservoir comprises two cylindrical portions
which protrude, respectively, from said lid and from said bottom thereof and being adapted to enter and lock selectively within said identical complementary connecting means of the venous reservoir or bag,
whereby the set of units is assemblable so as to constitute a device integrated in an extracorporeal blood circuit that has a configuration selectively including either said cardiotomy reservoir and venous reservoir or said cardiotomy reservoir and said venous bag.

2. The set according to claim 1, further comprising a scissor-like tool suitable to block said tube which protrudes from the cardiotomy reservoir.

3. The set according to claim 1, further comprising a blocking tap suitable to block said tube which protrudes from the cardiotomy reservoir.

4. The set according to claim 1, further comprising an oxygenation unit, said venous reservoir and venous bag being provided with further mutually identical connection means for monolithic connection thereof to said oxygenation unit.

5. The set of claim 4, wherein said oxygenation unit comprises a lid provided with a slot, said further identical connection means of the venous reservoir and of the venous bag for connection thereof to said oxygenation unit comprising each a tab which protrudes respectively from a bottom of the venous reservoir and from the rigid supporting base of the venous bag, said tab being adapted to enter said slot provided on said Lid of the oxygenation unit in order to be locked thereat.

6. An integrated device for an extracorporeal blood circuit, the device comprising three units that are constituted by a cardiotomy reservoir, an oxygenation unit and a selected one of a venous reservoir and a venous bag, wherein:
   the cardiotomy reservoir comprises connecting means;
   the venous reservoir comprises complementary connecting means that are shaped complementary to said connecting means of the cardiotomy reservoir;
   the venous bag comprises complementary connecting means thereof that are shaped complementary to said connecting means of said cardiotomy reservoir; and
   a tube is provided which protrudes from the cardiotomy reservoir and is adapted to selectively connect to the venous reservoir or to the venous bag; wherein:
   said venous bag comprises a rigid supporting base thereof and said venous reservoir comprises a lid and an outer enclosure,
   said complementary connecting means of the venous reservoir comprises a top ring and a bottom ring that are monolithically connected to said lid and, respectively, to said outer enclosure thereof, and
   said complementary connecting means of the venous bag comprises a top ring and a bottom ring that are monolithically connected to said rigid base,
the rings of the venous reservoir being respectively identical to the rings of the venous bag;
and wherein:
   said cardiotomy reservoir comprises a lid and a bottom,
   said connecting means of the cardiotomy reservoir comprises two cylindrical portions which protrude, respectively, from said lid and from said bottom and are adapted to enter and lock selectively within said identical rings forming the complementary connecting means of the venous reservoir or bag;
whereby the integrated device has a configuration selectively including either said cardiotomy reservoir, oxygenation unit and venous reservoir or said cardiotomy reservoir, oxygenation unit and said venous bag.

7. The device of claim 6, wherein said venous reservoir and venous bag are provided with further mutually identical connection means for monolithic connection thereof to said oxygenation unit.

8. The device of claim 7, wherein said oxygenation unit comprises a lid provided with a slot, said further identical connection means of the venous reservoir and of the venous bag for connection thereof to said oxygenation unit comprising each a tab which protrudes respectively from a bottom of the venous reservoir anti from the rigid supporting base of the venous bag, said tab being shaped so as to enter said slot provided on said lid of the oxygenation unit in order to be locked thereat.

* * * * *